US009339213B2

(12) United States Patent
Otsamo et al.

(10) Patent No.: US 9,339,213 B2
(45) Date of Patent: May 17, 2016

(54) MEASURING DEVICE AND METHOD FOR INDICATING LEVEL OF FATIGUE

(71) Applicant: Juno Medical LLC, Oulu (FI)

(72) Inventors: Katriina Otsamo, Oulu (FI); Timo Matalalampi, Oulu (FI)

(73) Assignee: Juno Medical LLC, Oulu (FI)

(*) Notice: Subject to any disclaimer, the term of this patent is extended or adjusted under 35 U.S.C. 154(b) by 0 days.

(21) Appl. No.: 14/386,678

(22) PCT Filed: Mar. 7, 2013

(86) PCT No.: PCT/FI2013/050251
§ 371 (c)(1),
(2) Date: Sep. 19, 2014

(87) PCT Pub. No.: WO2013/140030
PCT Pub. Date: Sep. 26, 2013

(65) Prior Publication Data
US 2015/0045693 A1    Feb. 12, 2015

(30) Foreign Application Priority Data
Mar. 23, 2012 (FI) .................................. 20125329

(51) Int. Cl.
*A61B 5/00* (2006.01)
*A61B 5/11* (2006.01)
(Continued)

(52) U.S. Cl.
CPC ............. *A61B 5/1104* (2013.01); *A61B 5/4519* (2013.01); *A61B 5/6825* (2013.01); *A61B 5/6826* (2013.01); *A61N 1/0456* (2013.01); *A61B 5/1107* (2013.01); *A61B 5/162* (2013.01)

(58) Field of Classification Search
CPC .. A61B 5/04; A61B 5/04001; A61B 5/04004; A61B 5/053; A61B 5/11; A61B 5/1104; A61B 5/1107; A61B 5/1124; A61B 5/103; A61N 1/18; A61N 1/36
See application file for complete search history.

(56) References Cited

U.S. PATENT DOCUMENTS 7,499,764 B2    3/2009 Fukui
9,138,161 B2 *  9/2015 Lading ............... A61B 5/02007
(Continued)

FOREIGN PATENT DOCUMENTS

WO         0213696       2/2002
WO       2011159883     12/2011

OTHER PUBLICATIONS

International Search Report and Written Opinion for PCT/FI2013/050251 dated Mar. 23, 2012.
(Continued)

*Primary Examiner* — Max Hindenburg
(74) *Attorney, Agent, or Firm* — Andrus Intellectual Property Law, LLP (57) ABSTRACT

Gradually strengthening electric stimulation impulses are sent to the median nerve at the wrist. Thereby an action potential caused on some level of the stimulation signal proceeds along the sensory nerve to the spinal cord, from where the nerve impulse (Hoffmann's reflex) returns via the alpha motor neuron pool along a motor nerve to a muscle and causes the movement of the muscle. This movement is detected by an accelerometer. The intensity of the stimulation signal and the time from the stimulation signal to the motoric response are saved, and by means of these the level of fatigue is evaluated. A device comprises a cuff with two electrodes and a current generator for forming impulses for the electrodes. The cuff can be placed on the wrist such that at least one of the electrodes is on the volar side of the hand at the point of the median nerve. The measuring device further comprises an accelerometer, that is provided to produce a signal, when the accelerometer detects a movement. The measuring device further comprises a control arrangement, which is provided for guiding the current generator to produce impulses and to monitor the signal of the accelerometer. The control arrangement stops the production of impulses, when the signal created by the accelerometer is detected, and saves the intensity value of at least the latest impulse and the time ΔT, which is the difference between the points of time of the signal produced by the accelerometer and said latest impulse. From these the value describing the level of fatigue can be calculated.

20 Claims, 6 Drawing Sheets

(51) Int. Cl.
*A61N 1/04* (2006.01)
*A61B 5/16* (2006.01)

(56) References Cited

U.S. PATENT DOCUMENTS

| | | | |
|---|---|---|---|
| 9,155,505 B2* | 10/2015 | Caduff | A61B 5/6831 |
| 2005/0283205 A1 | 12/2005 | Lee et al. | |
| 2010/0069796 A1 | 3/2010 | Duncan et al. | |

OTHER PUBLICATIONS

Finnish Search Report for Finnish Application No. 20125329 dated Nov. 30, 2012.

Beck T. W., et al., Does the frequency content of the surface mechanomyographic signal reflect motor unit firing rates? A brief review, Journal of Electromyography and Kinesiology, vol. 17, Nr. 1, pp. 1-13, Nov. 17, 2006.

Orizio C., et al., The surface mechanomyogram as a tool to describe the influence of fatigue on biceps brachii motor unit activation strategy. Historical basis and novel evidence., European Journal of Applied Physiology, vol. 90, Nr. 3-4, pp. 326,336, 2003.

Tarata M. et al., The accelerometer MMG measurement approach, in monitoring the muscular fatigue, Proceedings of the 3rd International Conference on Measurement, pp. 239-242, May 14, 2001.

Gobbo M., et al., Torque and surface mechanomyogram parallel reduction during fatiguing stimulation in human muscles, European Journal of Applied Physiology, vol. 97, Nr.1, pp. 9-15, May 1, 2006.

* cited by examiner

MEASURING DEVICE AND METHOD FOR INDICATING LEVEL OF FATIGUE

CROSS-REFERENCE TO RELATED APPLICATIONS

This application is the U.S. national stage application of International Application PCT/FI2013/050251, filed Mar. 7, 2014, which international application was published on Sep. 26, 2013, as International Publication WO2013/140030 in the English language. The international application is incorporated herein by reference, in entirety. The international application claims priority to Finnish Patent Application No. 20125329, which is incorporated herein by reference.

The invention relates to a measuring device for indicating level of fatigue, the measuring device comprising a cuff, where two electrodes, an anode and a cathode, and a power generator are provided to form pulses for the electrodes. Further, the invention relates to a method where said measuring device is used for indicating level of fatigue.

PRIOR ART

During physical exercise the level of fatigue of the neuromuscular system, experienced by an individual, varies. In order for the exercising to be effective, it is good to know what kind of physical stress the individual's neuromuscular system or a part of it was subjected to during the exercise. In addition to the level of fatigue, it is good to know about the recovery of the individual after the exercise performance carried out by the individual, whether it concerns a top-ranking athlete or an exerciser. If the individual does not recover after an exercise, he/she may end to a condition of so called overtraining due to excessive training. Thin may lead to a forced rest for weeks or up to several months. Especially, in regard to top-ranking athletes, overtraining due to exercising is very undesirable.

The individual's own subjective sensation of exertion and recovery thereafter has been found to be insufficient.

There are different measuring arrangements for measuring the state of fitness of an exercising individual. Aerobic fitness, i.e. the fitness related to heart, lungs and blood circulation, describes the amount of oxygen pumped and carried to the muscles by the heart, and the ability of the muscles to utilize the received oxygen. Aerobic fitness is especially related to endurance sports.

A heart rate monitor and its heart rate analyses may be used for measuring aerobic fitness. With a heart rate analysis the effect of several body events on the heart rate, controlled by the autonomic nervous system, is measured. Control of the autonomic nervous system may be disturbed through hard exercising or mental stress. The serious overstraining state, caused by exercising, is indicated in the autonomic nervous system also at rest.

Stress and overtraining are often shown with delay in the autonomic nervous system, and that's why exercising may have been too stressing for a longer time before one comes aware of the situation. Thereby, amending measures may be time-consuming.

One way of measuring an individual's fitness and recovery is to take blood samples often enough in connection with the exercises or after them. However, this way of measuring is difficult to be utilized. Moreover, measurements made from blood are complicated and expensive for an ordinary exerciser.

Recovery can be measured with extensive blood samples, where for example lactate and creatine kinase are measured. Lactate is a product of glucose metabolism, which is produced in the muscles especially as a result of anaerobic muscular activity. Creatine kinase is a common enzyme in muscle cells.

When a muscle is damaged because of exercising or for another reason, creatine kinase is released from muscle cells to blood. The larger the damage the more the measured value measured with a blood sample increases. In the same way, if an unexercised individual suddenly uses his/her muscles vehemently, soreness of the muscles related to it and a slight damage of a muscle increases the measured value of creatine kinase.

To optimize the end result of exercising the exercising individual needs to find the right proportion between exercising and recovering from it. In this way, fatigue and muscular damages due to hard exercising are prevented. Depending on the difficulty level of the exercise the exercising individual needs on an average from two days to two weeks to recover from a stressing exercise.

A change of an athlete's performance caused by such an exercise and recovery from it, as a result of which the performance is momentarily above the normal level, is called supercompensation. Thus, with a well-timed new exercise an ascending progress is accomplished in the training individual's performance.

The performed exercise and recovery from the exercise, in practice rest, play an important role in the supercompensation phenomenon. Exercising too early or too severely before recovering after the previous exercise leads to overtraining. In order to achieve supercompensation, the exercising individual needs to optimize his/her exercises such that the recovery time after the previous exercise is not too long or too short.

A nerve can be stimulated electrically with surface electrodes or needle electrodes. A stimulation stream travels from the positive electrode (anode) to the negative electrode (cathode). A negative charge formed close to the cathode causes depolarization and action potential of nerve fibres, which proceeds both in distal and proximal directions. In the area of the anode, correspondingly, a hyperpolarization takes place, which may weaken the nerve impulse proceeding in direction of the anode.

The H-reflex (Hoffmann's reflex) is a monosynaptic reflex that is produced when stimulating electrically the sensory nerve cells, triggered by the afferent nerve impulses coming to the spinal cord along the sensory nerves. By measuring the H-reflex, the whole reflex arc can be examined, which includes in addition to peripheral nerve fibres also a sensory dorsal root, the spinal cord and a motor anterior root. Because in measuring the H-reflex an external electrical stimulus is used, thereby the effect and activity of the sensory receptors of the muscle spindle and the other muscles are disregarded. Changes in measurement results indicate changes of sensitivity in the whole reflex arc. M-wave is a direct response of a muscle to stimulation of a motor nerve, i.e. a direct response from axon of alpha motor neuron.

A hand includes the median nerve that effects the innervation of the thumb, the forefinger, the middle finger and the middle finger side part of the ring finger. The median nerve is on the palm side at the wrist.

The publication U.S. Pat. No. 7,499,764 discloses an automatically functioning muscle stimulation system. This includes electrodes that give electric signals to the muscle, and a sensor that measures the size and speed of the movement of the muscle. The system according to the publication is self-adapted according to the results measured by the sensor. The publication discloses an embodiment where the system monitors the muscular exertion during the stimulation of the muscles by following the transition in the fusion frequency. The fusion frequency is measured before the stimulation of the muscles and it is repeated during the stimulation programme. When the fusion frequency has fallen to a certain part of the original value, the muscle has achieved some level of exertion. The fusion frequency is obtained, when the time T between the stimulation signals of the stimulation device is shortened, until the sensor does not detect a mechanical response of the muscle. This distance of the signals is the cycle time T of the fusion frequency. The fusion frequency is proportional to the exertion level of the stimulated muscle. Thus, in the publication, the electric stimulation is regulated until no measurable reaction can be obtained from the muscle. This can be very unpleasant for a strained muscle.

Publication US 2010/0069796 discloses a method, where it is monitored, whether a functional stimulation of muscles (FES, Functional Electrical Stimulation) i.e. a method, where it is strived to make the muscles to contract and relax on a functional level, has caused overstraining of muscles. In the method, equivalent electrical impulses are sent to the muscle and observed whether the response of the muscle is similar to each impulse. If the response is decreased, i.e. the muscle isn't able to react to the same signal as intensively as before, the muscle is considered to be strained. Also here, the muscle is being strained in order to find out whether it is strained.

SUMMARY

The object of the invention is a solution, by which the disadvantages and drawbacks of the prior art can be diminished. Particularly, the object of the invention is a solution by means of which the level of fatigue of physical exercising and the recovery level after training could be determined with an electrical measuring device quickly and reliably without straining the muscle or without need to use measuring electrodes.

The objects according to the invention are achieved through a device and a method, characterized in what is disclosed in the independent claims. Some preferred embodiments of the invention are disclosed in the dependent claims.

Inventors have discovered that generation of an H-reflex is proportional to the total level of fatigue which has been caused by exercising or other use of the muscular system. An electrical stimulus, i.e. the size of the electrical impulse that creates the H-reflex, and the time from the stimulus in question to detecting the H-reflex, change along with the change of the level of fatigue. Thus, by means of these, the level of fatigue can be evaluated. Along with growing of the level of fatigue, also the intensity of the current needed for developing the H-reflex grows. Also said time difference has been found to grow along with the growing of the level of fatigue. Time difference is also used to recognize the H-reflex, i.e. to distinguish it from local M-waves and other movements detected by the accelerometer, such as for example so called long lantency waves.

The main idea of the invention is to send gradually strengthening electric stimulation impulses to the median nerve at the wrist. Thereby, an action potential caused on some level of the stimulation signal proceeds along the sensory nerve to the spinal cord, from where the nerve impulse (Hoffmann's reflex) returns via the alpha motor neuron pool along a motor nerve to the abductor pollicis brevis muscle and causes the movement of the muscle. This movement, i.e. the H-reflex, is detected with an accelerometer that is connected to the device sending electric stimulation impulses. The intensity of the stimulus or impulse and the time from the stimulus to the motoric response is saved, and by means of these the level of fatigue is evaluated.

In a measuring device according to an embodiment of the invention, for indicating the level of fatigue there is a cuff with two electrodes, anode and cathode, and a current generator to provide impulses for the electrodes. A cuff is a part to be wrapped or placed in another way, for example, by slipping, around the wrist. According to a preferred embodiment of the invention, the cuff is provided in a way that it can be placed onto the wrist such that at least one of the electrodes is on the volar side of the hand at the point of the median nerve, and the measuring device further comprises an accelerometer, that is provided to produce a signal when the accelerometer detects a movement. The measuring device further comprises a control arrangement, which is provided for controlling the current generator to produce impulses, so that the intensity of the impulses grows proportionally to time, and to monitor the signal of the accelerometer. Moreover, the control arrangement is provided to stop the production of impulses, when the signal created by the accelerometer is detected, and to save the intensity value of at least the latest impulse and the time $\Delta T$, which is the difference between the points of time of the signal produced by the accelerometer and said latest impulse.

In an embodiment of the measuring device according to the invention, the current produced by the current generator is alternating current. In a second embodiment of the measuring device according to the invention, the current produced by the current generator is direct current. In a third embodiment of the measuring device according to the invention, the signals produced by the current generator are of constant length. In a fourth embodiment of the measuring device according to the invention, the signals produced by the current generator have constant frequency, i.e. the time difference between two successive signals is essentially constant.

In a fifth embodiment of the measuring device of the invention, the cuff is provided to go around the wrist, and the electrodes are placed in a way, that one electrode is on the dorsal side of the hand. In a sixth embodiment of the measuring device of the invention, the electrodes are placed in the cuff in a way that when the cuff is in its position, both electrodes are on the volar side of the hand essentially one after another in direction of the median nerve.

In a seventh embodiment of the measuring device of the invention, the measuring device comprises a part that extends to some finger of the hand where the cuff is attached, and the accelerometer is in this part. In an eighth embodiment of the measuring device according to the invention, the finger is the thumb, the forefinger or the middle finger, and the said part of the measuring device is arranged to go around the finger in question. The H-reflex is most clearly indicated in these fingers.

In a ninth embodiment of the measuring device according to the invention, the signal produced by the accelerometer is the H-reflex caused by the stimulation of the median nerve.

In a tenth embodiment of the measuring device according to the invention the control arrangement comprises a calculating unit for calculating the value of fatigue at least by means of the saved intensity value of the impulse or the time $\Delta T$ or both and for comparing it/them with the reference value. The reference value represents the value of fatigue which has been measured when the object is in a relaxed or recovered state, i.e. there is no noteworthy level of fatigue in the muscular system. The reference value can also be produced statistically. The difference between said value of fatigue and the reference value indicates the level of fatigue and its type. In other words, the greater is the difference between the value of fatigue and the reference value, the greater is the type of the level of fatigue. The level of fatigue can be classified in several different ways. In an eleventh embodiment of the measuring device according to the invention, the measuring device comprises an arrangement for indicating the type of the level of fatigue.

In a twelfth embodiment of the measuring device according to the invention, the measurement device comprises an interface unit for transmitting at least the saved intensity value of the impulse and the time ΔT to an external device. In a thirteenth embodiment of the measuring device according to the invention, the measuring device comprises a clock for determining the time, and the interface unit transmits furthermore the point of time of said saved impulse.

In a fourteenth embodiment of the measuring device according to the invention, the control arrangement is provided to detect the H-reflex by means of the time ΔT. In a fifteenth embodiment of the measuring device according to the invention, ΔT is 10-100 ms, i.e. the signals produced by the H-reflex fall into this time slot.

In a method according to an embodiment of the invention, for indicating the level of fatigue a measuring device is used, comprising a cuff, where two electrodes, an anode and a cathode, and a current generator are provided to form impulses for the electrodes. According to a preferred embodiment of the invention, the measuring device further comprises an accelerometer that is provided for producing a signal, when the accelerometer detects a movement. The method comprises steps where the cuff is placed onto the wrist in a way that at least one of the electrodes is on the volar side of the hand at the point of the median nerve, the current generator is guided to produce impulses, and it is monitored, whether the accelerometer is producing a signal. The method further comprises steps in which the intensity of the impulses is grown in relation to the time, and the production of impulses is stopped when the signal produced by the accelerometer is detected. At least the intensity value of the latest impulse and time ΔT, which is the difference between the points of-time of the signal produced by the accelerometer and said latest impulse, are saved and the H-reflex is identified by means of the time ΔT. By means of said values the value of fatigue is calculated that is compared with the reference value, and the difference between said value of fatigue and the reference value indicates the level of fatigue.

In an embodiment of the method according to the invention, the size of the difference between said value of fatigue and the reference value describes the type of the level of fatigue.

In a second embodiment of the method according to the invention, the type of the level of fatigue is presented in a measuring device or an external device with an arrangement for connection with the measuring device, or in both.

In a third embodiment of the method according to the invention, the ΔT caused by the H-reflex is 10-100 ms.

An advantage of the invention is that by means of it the level of fatigue of the object can be evaluated quickly and easily.

An advantage of the invention is that it can be used without a trained operator. Furthermore, the object of the measurement can use it by himself/herself.

An advantage of the invention is further, that it does not require stressing the muscle in order to examine the fatigue.

Further, an advantage of the invention is that therewith a device is provided that is easy to be carried along.

An advantage of the invention is also that it enables optimizing the training by avoiding a state where one has no time to recover after the state of fatigue.

DESCRIPTION OF THE FIGURES

In the following, the invention will be described in detail. In the description, reference is made to the enclosed drawings, in which.

DETAILED DESCRIPTION OF FIGURES

The embodiments in the following description are given as examples only, and a person skilled in the art may realise the basic idea of the invention also in some other way than what is described in the description. Though the description may refer to a certain embodiment or embodiments in several places, this does not mean that the reference would be directed towards only one described embodiment or that the described characteristic would be usable only in one described embodiment. The individual characteristics of two or more embodiments may be combined and new embodiments of the invention may thus be provided.

Figure 1:
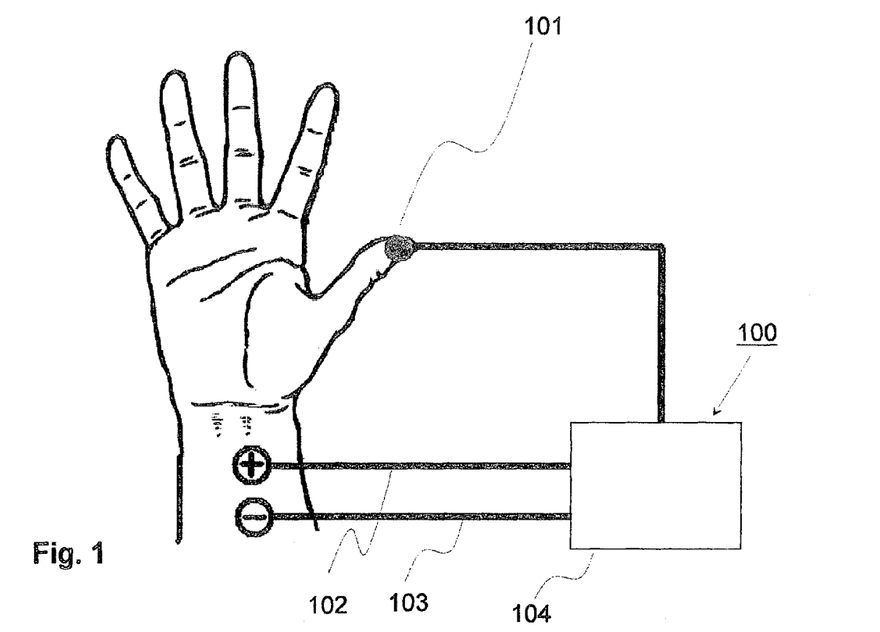
FIG. 1 shows by way of example a device according to the invention.

In FIG. 1 is shown by way of example a measuring device 100 according to the invention for indicating level of fatigue. The measuring device 100 comprises a central unit 104 which includes the parts related to the functioning of the measuring device, and two electrodes connected to the central unit, a first electrode 102 and a second electrode 103, and an accelerometer 101.

FIG. 1 shows the electric connection of the measuring device 100 with the hand: the accelerometer 101 is attached to the thumb, the electrodes, according to the Figure, the second electrode 103 or cathode proximally, and the first electrode 102 or the anode distally at the point of the median nerve on the wrist. Proximal is closer to the middle point, that is, closer to the spine. To facilitate placement of the electrodes they are attached to the cuff (not shown in FIG. 1) that can be placed onto the wrist, for example, by slipping or tightening. The cuff comprises instructions about its position of use, or it is formed such that when it is in its place at the wrist, at least one electrode is at the point of the median nerve.

The central unit 104 of the measuring device 100 produces stimulation impulses for the electrodes. The impulses get stronger with time, and their production is stopped, when the signal of the accelerometer is detected, i.e. that the accelerometer has been in motion. Preferably, a limit value is set for the signal, after exceeding of which the reading of the accelerometer is interpreted as a signal.

By gradually increasing the intensity of the stimulation impulses, first the H-reflex is obtained, because the sensory nerve cells react to a lower intensity of stimulus than the motor nerve cells. While increasing the intensity of the stimulus, also the M-wave appears, and while further increasing the stimulus the H-reflex disappears. Because the M-wave travels a shorter way than the H-reflex, the response time of the M-wave is shorter than the one of the H-reflex. Consequently, the H-reflex can be distinguished from the M-wave, when the time between the stimulation impulse and the response is known. In the measurements, there may also be seen so called long latency waves that have a longer response time than the H-reflex. Researchers have noticed the H-reflex to appear when the time difference between the stimulation impulse and the signal of the accelerometer is in the range of 10-100 ms. Thereby, signals outside that range are not caused by the H-reflex.

The measuring device 100 is provided such that the electrodes stimulate the median nerve, which stimulation with growing of irritation produces the H-reflex that makes the fingers of the hand in question, and especially the thumb, the forefinger and the middle finger, to move. The accelerometer 101 can be placed onto a finger, or alternatively close to the electrodes, because moving of fingers in the H-reflex also moves the rest of the hand, which movement is detectable by the accelerometer 101. When the H-reflex is detected, i.e. the accelerometer 101 has produced a signal, the measuring device saves the intensity of the stimulation impulse and the time difference between the points of time of the impulse in question and the signal of the accelerometer. The series of events from the first stimulation impulse until saving of the results is called a measurement event. A measurement event may include even several of the described series of events.

Figure 9:
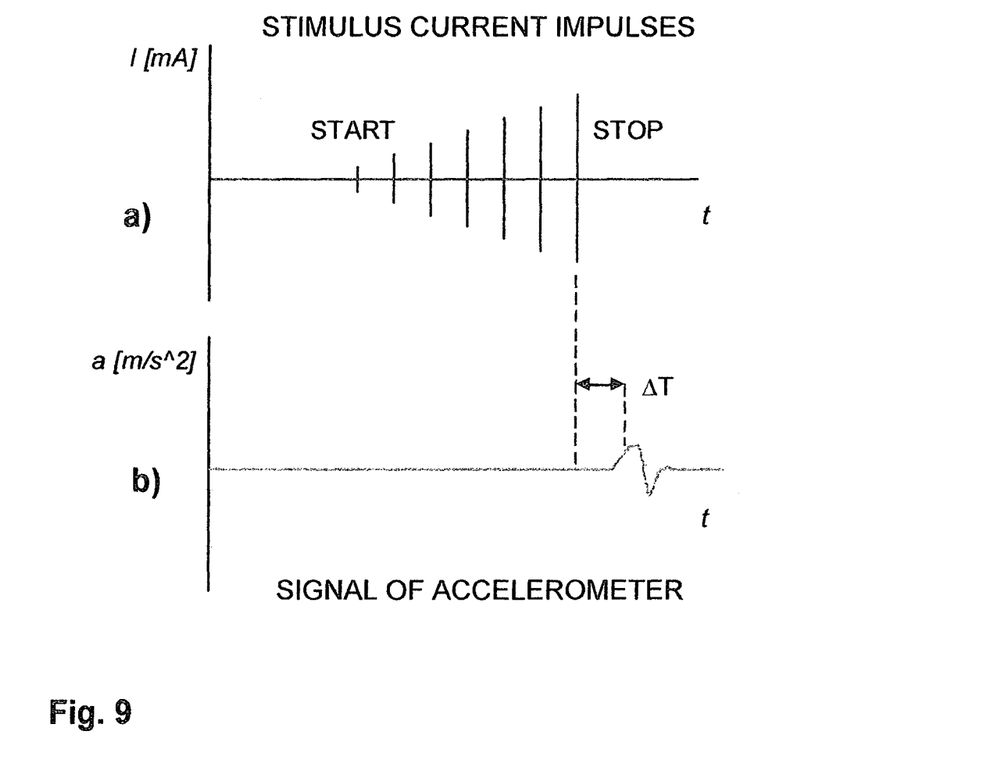
FIG. 9 shows an example of a current impulse sequence, formed by the device, and a signal of the accelerometer in relation to time.

FIG. 9 shows an example of one measurement event performed with a device and method according to the invention. At point a) there is a current-time coordinate system, where a series of stimulation impulses is shown, where the intensity of successive impulses increases as a function of time. At point b) there is the signal of the accelerometer in the acceleration-time coordination system. When the signal of the accelerometer is detected, the production of stimulation impulses is stopped. The time difference between the last impulse and the signals of the accelerometer is $\Delta T$. The stimulation impulses are naturally not grown unlimitedly, but there is a limit value, at which the measurement event is stopped even if the signal of the accelerometer was not detected.

Figure 2:
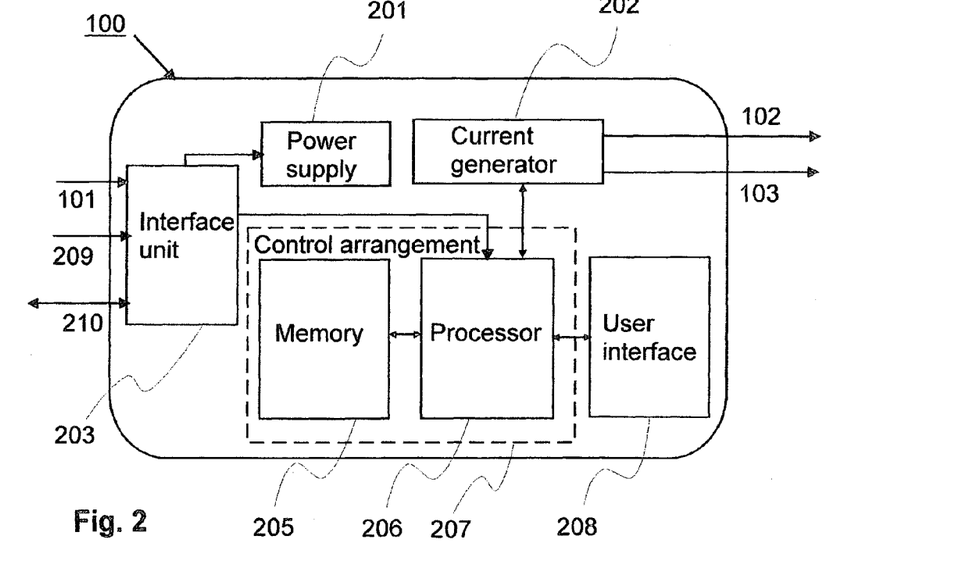
FIG. 2 shows the device of FIG. 1 in a block diagram.

FIG. 2 shows in more detail the measuring device 100 according to the invention for indicating level of fatigue, shown in FIG. 1. The measuring device 100 comprises a power supply 201 for satisfying the electric power needed by control arrangement 207, user interface 208 and current generator 202. The power supply 201 can preferably be an accumulator or a battery.

The measuring device 100 comprises preferably also an interface unit 203. The interface unit 203 comprises means, through which the accumulator of the power supply 201 can be charged from an external power supply 209. The interface unit 203 further comprises means with which the measuring device 100 according to the invention can be connected to an external data processing machine 210. Data transfer to this external data processing machine 210 can be performed either via a cable or with a wireless data access. A wireless data access can be realized, for example, with an infrared or a Bluetooth connection or similar. The interface unit 203 further comprises means, through which the measuring device 100 according to the invention is connected to the accelerometer 101 on the individual to be examined.

The central unit 104 of the measuring device 100 preferably comprises also a user interface 208. The user interface 208 preferably comprises regulation/control means that the functioning of the device can be controlled. These regulation means can be, for example, regulating knobs, slide switches or function keys on a touch screen. Further, the user interface 208 preferably comprises display means, with which the measurement results can be displayed during the measurement event or thereafter. These display means can be a light arrangement where, for example, a light of different colour is switched on, the light indicating the type of the level of fatigue. For example, if the object is found to be recovered, a green light is switched on, and if a level of fatigue is detected, a red light is switched on. Level of fatigue can further be indicated by a flickering light. The central unit can also be arranged such that it does not comprise actual display means in itself, but the level of fatigue is indicated with an external data processing machine 210, to which the measuring device has a data transfer connection. Functions of the measuring device can thus be divided to several devices.

The control arrangement 207 of the measuring device 100 preferably comprises a suitable processor 206 or a programmed logic and a memory 205 connected to it. In the memory 205 either a non-volatile and/or a volatile memory technology can be utilized. The computer programme to be utilized in an arrangement for indicating level of fatigue according to the invention is preferably saved in the memory 205. The processor 206, the memory 205 and the computer programme saved in the memory 205 are provided for determining and indicating on the basis of the performed measurements the actual state of the muscular system. Also measurement results describing the level of fatigue and/or recovery of the muscular system can be stored in the memory 205, at least temporarily. The control unit can comprise a calculating unit which in the example works in the above described processor 206 and memory 205. The calculating unit calculates the value of fatigue from the measured values. A reference value that describes the value of fatigue of the object in a relaxed or recovered state, i.e. a state where the muscular system is not essentially strained, has been saved in the memory 205. The control arrangement does not necessarily have to include a calculating unit, but the measured values are transmitted to an external data processing machine 210 that performs the calculations. The value of fatigue can be the value of the current of the stimulation impulse or it can be the mathematically processed result of values of the currents of the stimulation impulses of several measurement events, such as for example, an average value. For calculation of the value of fatigue, in addition to the current value, also the time difference between the stimulation impulse and the accelerometer can be used.

The control arrangement 207 receives the necessary control commands from the user interface 208. With these control commands the functioning of the measuring device 100 is preferably controlled. The measurement event can be started and stopped with the given control commands. The control arrangement 207 can receive also control commands sent from an external data processing machine 210 that are obtained through the interface unit 203. Further, the control arrangement 207 can send through the interface unit 203 to an external data processing machine 210 information about the fact when the measurement was performed and what kind of measurement results were obtained.

The current generator 202 can form a stimulation current according to the control command received from the control arrangement 207. The current generator 202 modifies the intensity of the stimulation current to correspond to the received control command. After receiving a measurement command, given by the user by means of the user interface 208, the current generator 202 guides the stimulation current impulse via electrodes 102 and 103 to the part of the neuromuscular system being the object of measurement. At least one of the electrodes is at the wrist on the volar side or the palm side, at the point of the median nerve. The current impulse can be formed by alternating current or direct current. Current impulses are sent in series. The current impulses of a series are preferably sent at constant intervals. The measuring device 100 can also be provided such that the current impulses have different intervals, for example current impulses that have exceeded a certain current intensity have a different time interval than the ones below the current intensity in question. The interval of the current impulses is preferably such that the H-reflex caused by a current impulse can be detected before sending the next current impulse, or that the current impulse caused by the H-reflex can be identified. For example, if $\Delta T$ is so short, that the travel time of the reflex would be physically impossible, the second last impulse is selected. Intensity of current impulses in the series increases in relation to time. To reduce uncertainty factors and to minimize failures, it is naturally possible to form several impulses with the same intensity in succession.

Figure 8:
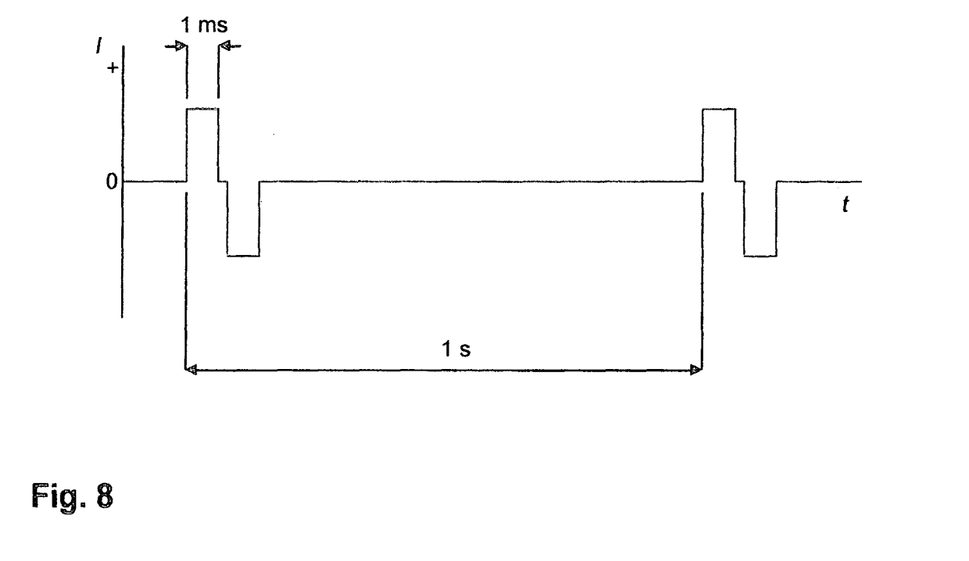
FIG. 8 shows an example of a current impulse formed by the device according the invention.

In FIG. 8 there is an example of a current impulse produced by a measuring device according to the invention. In this example, the duration of the impulse is 1 ms (positive phase), and the frequency of the impulses is 1 Hz, that is, they are repeated at intervals of one second. Naturally, also other values can be used. The impulses shown in the Figure are of equal size. For example, the' next two impulses can be of greater intensity and the next two again greater. It is possible that the amount of signals, essentially of equal size, repeated in the measurement event varies, that is, for example after the above-mentioned impulses there will come four equal impulses, more intense than the previous impulses.

The control arrangement 207 monitors, whether the accelerometer 101 gives a signal during the measurement event. When a signal is detected, the control arrangement 207 stops the production of current impulses and saves in the memory 205 the intensity value of the latest current impulse and the time difference $\Delta T$ between the time of sending that current impulse and the point of time of the signal detected by the accelerometer. Instead of the time difference $\Delta T$ also the points of time in question can be saved. By means of these results the control arrangement 207 can calculate the value of fatigue. Limit values can be given to the signal of the accelerometer 101, where for example too small and too great values are rejected. The limit values are calculated such that they eliminate incorrect results. After a rejected result of the accelerometer the measuring event can either be continued or it can be started from the beginning. In order to minimize failures, the measuring event can be repeated several times, and the results can be processed with a mathematical method. The measurement is also rejected, if the time difference $\Delta T$ is not in the given range, i.e. it is not the H-reflex.

Figure 3:
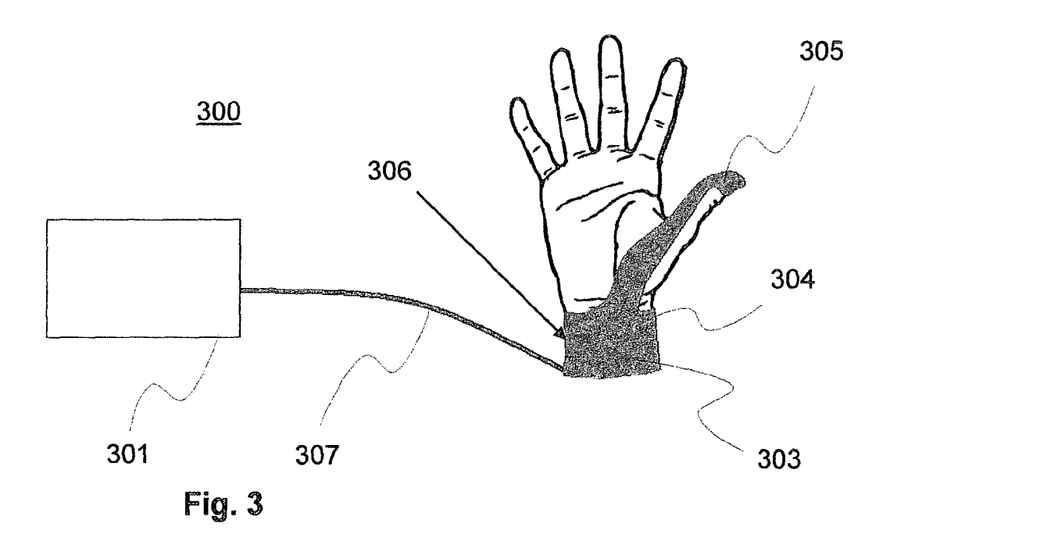
FIG. 3 shows by way of example a second device according to the invention.

FIG. 3 shows another example of the measurement device 300 according to the invention. The measurement device 300 comprises a central unit 301 which includes the parts related to the functioning of the measurement device, and two electrodes connected to the central unit, a first electrode 303 and a second electrode 304, and an accelerometer 305. The measuring device 300 further comprises a cuff 306. Said electrodes and accelerometer are attached to the cuff. The cuff is of fabric or plastic or combination thereof or of similar material, which is preferably elastic. It goes around the wrist and can be put in its position, for example, by slipping the hand through the cuff by stretching the elastic material of the cuff. When the cuff is in its position, the stretching can be relaxed, and the cuff takes its position such that the electrodes are placed at their measuring points. In the case according to the example, the electrodes are one after another on the palm side of the wrist in direction of the median nerve such that at least one of the electrodes is at the point of the median nerve for its stimulation. The cuff can also be an elongated piece that is put in its place at the wrist and tightened, for example, with a buckle, Velcro tape or similar. The cuff may include an instruction, for example a form or a marking that guides to place the cuff in the right position.

In the example of FIG. 3, the cuff 306 comprises a finger part that extends to a finger of the hand that the cuff is attached to, such that said finger, part can be attached to the finger in question. The accelerometer 305 is, in this finger part. The finger part is formed in a way that the accelerometer can be put tightly in its place, so that it cannot move and thus cause incorrect signals. In the example this has been realized in a way that the finger part comprises a hood that can be pulled on the finger such that the finger part is tightened and presses the accelerometer in its position. Material of the finger part may differ from the cuff material.

The central unit 301 is connected to the electrodes in the cuff 306 and to the accelerometer with a connecting cable 307. In this case, the central unit is apart from the cuff, but the central unit can also be integrated with the cuff, whereby an actual connecting cable is not necessary. The accelerometer can also be apart from the cuff.

Figure 4:
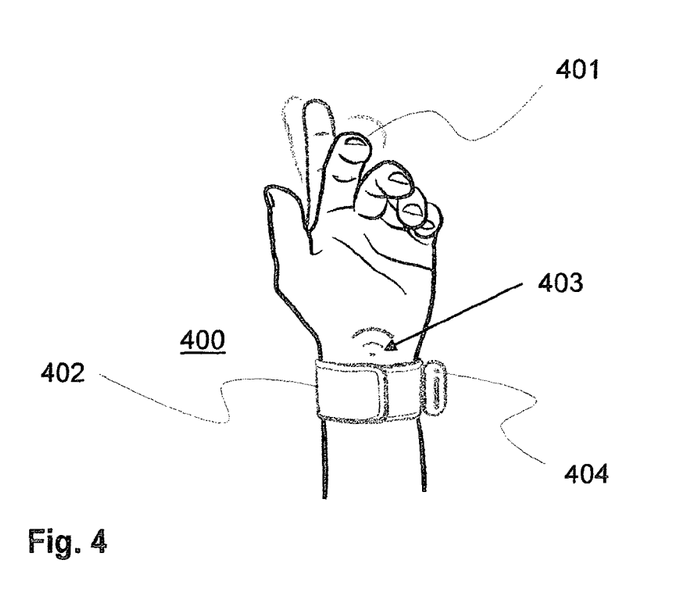
FIG. 4 shows by way of example a third device according to the invention.

FIG. 4 shows a third example of the measuring device 400 according to the invention. Here, the parts of the measuring device, the central unit, the electrodes and the accelerometer, are integrated to the cuff. Thereby, in order to make the measuring device smaller, for example, the indication of level of fatigue can be excluded, and instead of that, the value of the level of fatigue and the measurement results are transmitted with connection 403 that is preferably wireless, to an external device that then indicates the level of fatigue. Functions of the central unit can thus be divided to several devices.

Because the wrist moves under the influence of the H-reflex less than the fingers, the accelerometer is in the example of FIG. 4 provided to produce a signal at a smaller movement, or the control arrangement reacts or stops the measurement event at a smaller signal than in the embodiment, where the accelerometer is in the finger.

Figure 5:
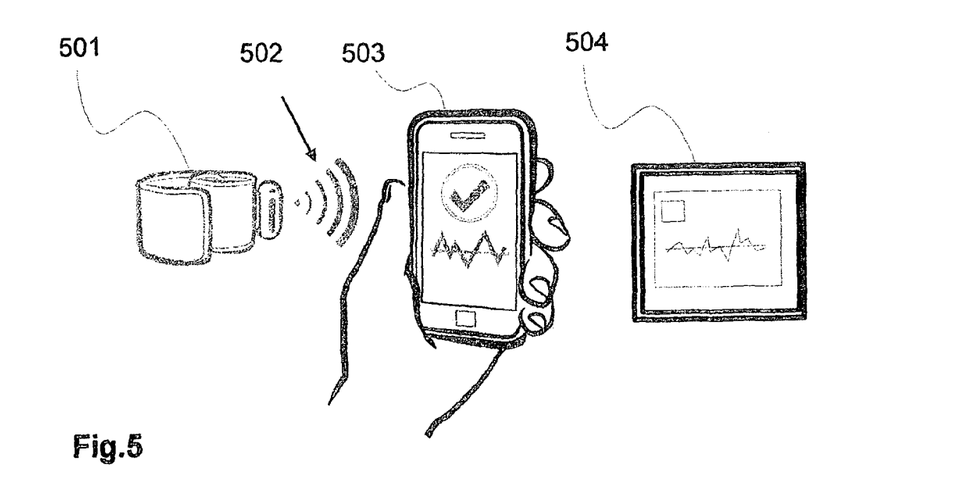
FIG. 5 shows an example of use of a device according to the invention.

FIG. 5 shows an example of an arrangement, where the measuring device 501 transmits with a wireless connection 502 measurement results to the first external device 503, which in this example is a smart phone. The first external device is provided to show the type of the level of fatigue, either calculated by the measuring device or calculated by the first external device from the results sent by the measuring device. Although hereby the measuring device and the first external device are shown separately, however, these together realize the measuring device according to the invention for indicating level of fatigue. The results measured and/or calculated by the measuring device 501 can be transmitted also to several devices, such as to another external device 504 of the example in FIG. 5, which is a tablet machine. Different devices can perform different types of tasks. The first external device can, for example, indicate the actual level of fatigue, and the second external device can save measurement results from a longer time and process them with a statistical method.

Figure 6:
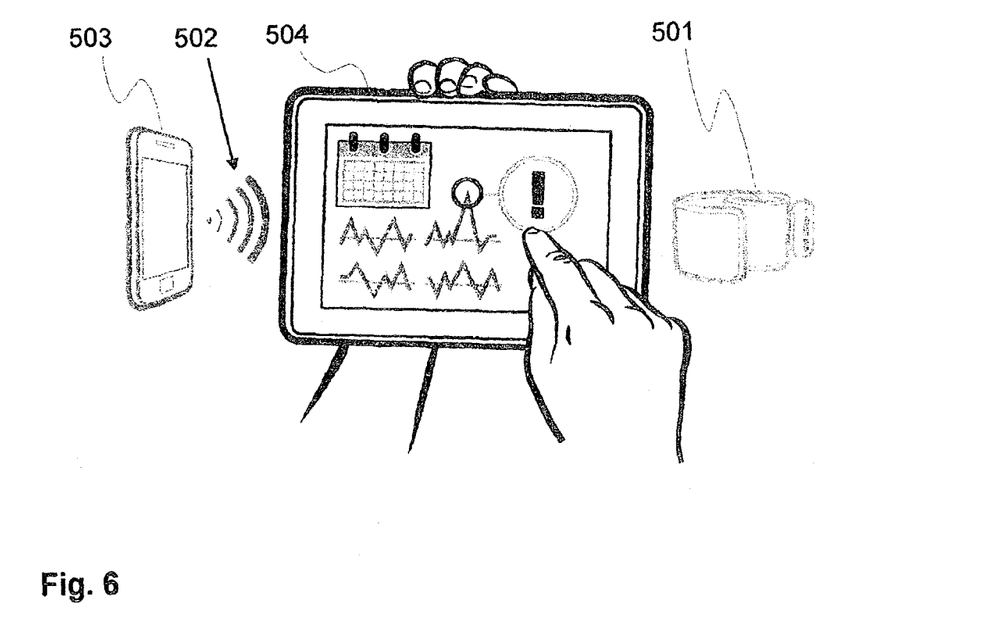
FIG. 6 shows another example of use of a device according to the invention.

In FIG. 6, another example is shown about processing the results of the measuring device 501 with external devices. The results measured by the central unit 501 are transmitted to the first external device 503 that further transmits the results to another external device 504. Now the other external device is provided for receiving results from several first external devices 503 or several measuring devices 501. Thus, for example, the trainer of the team can monitor the convenience of the training and resting of the players of the team.

Figure 7:
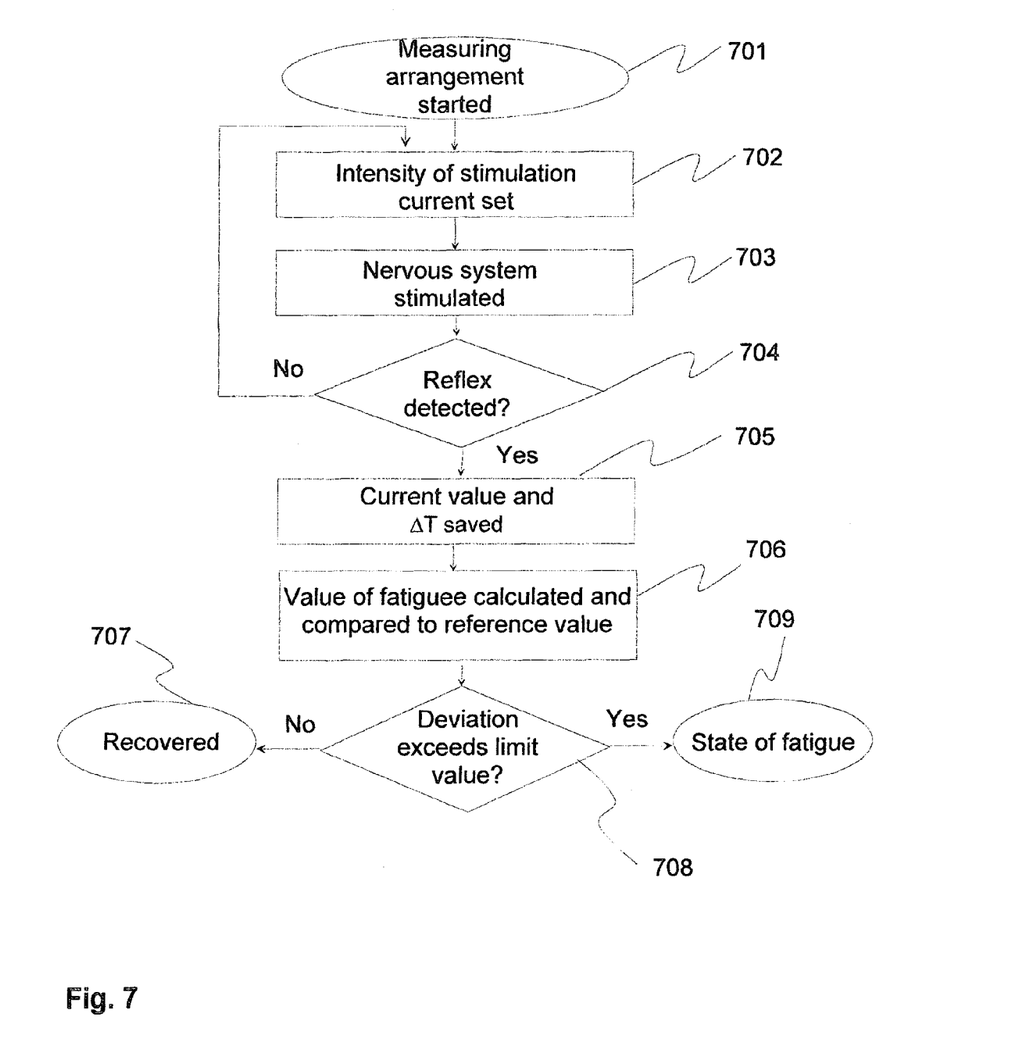
FIG. 7 shows in an exemplary flow chart some main steps of the measuring method according to the invention, indicating recovery.

FIG. 7 shows by way of example a flow chart of the method according to the invention. Hereby the method is described step by step.

Measurement of the neuromuscular system is started at 701. The cuff of the measuring device is put on the wrist in a way that the electrodes are put on their positions, whereafter the measuring device is started.

At 702 the intensity of the stimulation current, used in the calculation, is selected. If the measurement event begins with this measurement, the first impulse is determined, the intensity of which is saved in the memory of the measuring device.

While the measuring is running, the intensity of the stimulation current is grown or it is kept unchanged. Naturally, there is a limit in the intensity of the stimulation current, that is not exceeded, but the measurement event is interrupted, if that limit is achieved.

At step 703 the neuromuscular system is stimulated with an impulse determined at step 702.

If at step 704 a reflex is detected, that is the accelerometer produces a signal that is interpreted to be caused by the H-reflex, the current value or the intensity of the impulse that caused the detected H-reflex, and the time difference between detecting the H-reflex and sending the impulse in question are saved at step 705. If again the impulse did not result in a reflex, that is, it did not move the accelerometer in a way that it would have caused a signal, one returns to step 702 where according to the instructions either the stimulation current is increased or the previous impulse is repeated.

At step 706 the value of fatigue is calculated from the measurement results, and it is compared to the individual reference value in the memory, describing a relaxed and recovered state. The reference value can be a measurement result or it can be a statistical quantity that is determined, for example, by the size and muscle mass of the object to be measured. The reference value may also be a dynamic variable, such as a long term average of the resting state. At step 708 it is checked, how much the value of fatigue differs from the reference value. If the difference between the value of fatigue and the reference value exceeds a limit value, the object is interpreted to be in a state of fatigue 709. If again the, difference between the value of fatigue and the reference value does not exceed the limit value in question, it is interpreted that the object has recovered from the state of fatigue 707. On basis of the size of the deviation the state of fatigue can be classified into different types.

Figure 10:
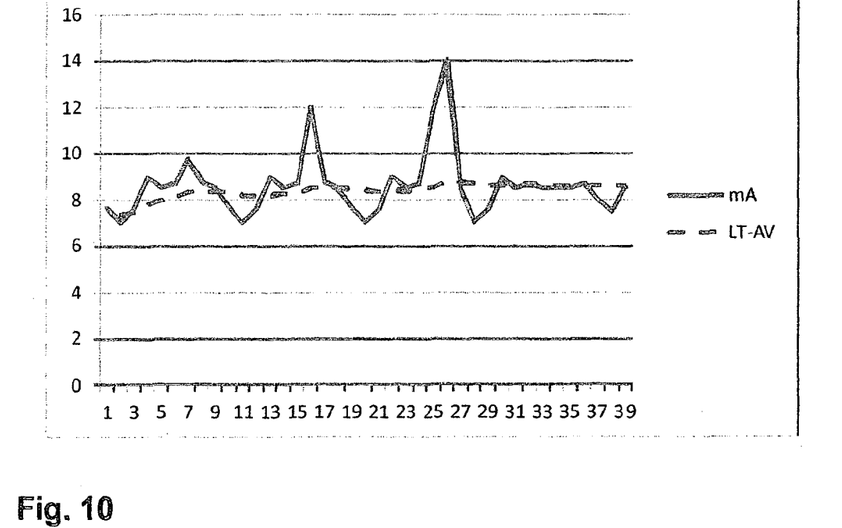
FIG. 10 shows an example of measurement results obtained by the device and the method according to the invention.

FIG. 10 shows an example of measurement results obtained by the device and the method according to the invention. The results are shown in a current-time coordination system. On the Y-axis there is the intensity of the saved current, i.e. the intensity of the current impulse, that has caused the H-reflex, and on the X-axis there is the time. Time units may be, for example, periods of twenty-four hours.

In this example, the user, for example an athlete, performs the measurement at a standardised time, for example, in the morning before the exercises of the day, whereby the measurement result is comparable with the previous measurement results. The continuous graph is the value of fatigue, and the diagram shown in broken line is the reference value, which is the long time average (LT AV, Long time average) of the resting state measurements. Also a constant value can be used as a reference value. The difference between the value of fatigue and the reference value represents the level of fatigue. The exercise performed by the athlete shows as a spike upwards in the diagram. The spike is followed by recovery to the long term average, which means that there is no such stress of the neuromuscular system left that would not recover. This occurs for example at the point of time 26.

Figure 11:
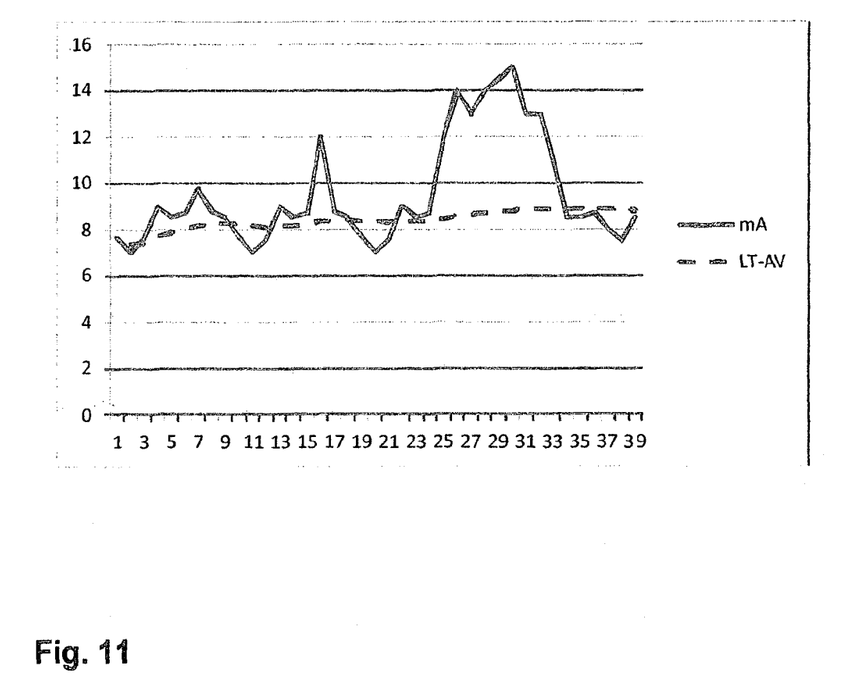
FIG. 11 shows another example of measurement results obtained by the device and the method according to the invention.

FIG. 11 shows another example of measurement results obtained by the device and the method according to the invention. The coordinate system corresponds to the one in FIG. 10. Hereby, the exercise performed by the athlete is shown as a spike upwards, but the spike isn't followed by recovery back to the long term average, but the stress stays unrecovered. Several successive measurement results that differ from the long term average, indicate stress that is not recovered from and leads later to overstrain. On basis of researches of the inventors, an accumulated stress of about three days that doesn't have time to get recovered from, that is, the athlete continues exercising with too hard intensity, shows as an occurred overstrain also in other indicators of performance. This can be seen at the points of time 26-32.

Above, some preferred embodiments according to the invention have been described. The invention is not limited to the solutions described above, but the inventive idea can be applied in numerous ways within the scope of the claims.

The invention claimed is:

1. A measuring device for indicating level of fatigue, the measuring device comprising a cuff with two electrodes, anode and cathode, and a current generator which is arranged to form impulses for electrodes, wherein the cuff is provided in a way that it can be placed on the wrist such that at least one of the electrodes is on the volar side of the hand at the point of the median nerve, and the measuring device further comprises an accelerometer that is provided to produce a signal when the accelerometer detects a movement, and the measuring device further comprises a control arrangement that is provided
   to guide the current generator to produce impulses and to monitor the signal of the accelerometer,
   to grow the intensity of the impulses in regard to time,
   to stop producing impulses, when the signal produced by the accelerometer is detected,
   to save at least the intensity value of the latest impulse and time $\Delta T$, which is a difference between a time of the signal produced by the accelerometer and a time of the latest impulse, and
   to calculate a level of fatigue based on at least one of the intensity value of the latest impulse and the time $\Delta T$.

2. The measuring device according to claim 1, wherein the current produced by the current generator is alternating current.

3. The measuring device according to claim 1, wherein the current produced by the current generator is direct current.

4. The measuring device according to claim 1, wherein the signals produced by the current generator are of a constant length.

5. The measuring device according to claim 1, wherein the signals produced by the current generator have a constant frequency, i.e. the time difference between two successive signals is essentially constant.

6. The measuring device according to claim 1, wherein the cuff is provided to go around the wrist, and the electrodes are placed in a way, that one electrode is on the dorsal side of the hand.

7. The measuring device according to claim 1, wherein the electrodes are placed in the cuff such that when the cuff is in its position, both electrodes are on the volar side of the hand essentially one after another in direction of the median nerve.

8. The measuring device according to claim 1, wherein the measuring device is provided such that it comprises a part that extends to a finger of the hand that the cuff is attached to, and the accelerometer is in this part.

9. The measuring device according to claim 8, wherein the part is configured to extend to a thumb, a forefinger or a middle finger of the hand.

10. The measuring device according to claim 1, wherein the signal produced by the accelerometer is the H-reflex caused by stimulation of the median nerve.

11. The measuring device according to claim 1, wherein the control arrangement comprises a calculation unit for calculating a value of fatigue based on at least the saved intensity value of the impulse or the time $\Delta,T$ or both, and for comparing it/them with a reference value, and the difference between the value of fatigue and the reference value indicates the level of fatigue.

12. The measuring device according to claim 11, wherein the measuring device comprises an arrangement for indicating the type of the level of fatigue.

13. The measuring device according to claim 1, wherein the measuring device comprises an interface unit for transmitting at least the saved intensity value of the impulse and the time $\Delta T$ to an external device.

14. The measuring device according to claim 13, wherein the measuring device comprises a clock for determining the time of the impulse, and the interface unit transmits furthermore the time of the latest impulse.

15. The measuring device according to claim 10, wherein the control arrangement is provided for recognizing the H-reflex based on the time $\Delta T$.

16. The measuring device according to claim 15, wherein $\Delta T$ is 10-100 ms.

17. A method for indicating level of fatigue, in which method a measuring device is used that comprises a cuff-where there are provided two electrodes, an anode and a cathode, and a current generator which is provided to form impulses for electrodes, wherein the measuring device further comprises an accelerometer that is provided to produce a signal; when the accelerometer detects a movement, and the method comprises:

placing the cuff onto the wrist in a way that at least one of the electrodes is on the volar side of the hand at the point of the median nerve, guiding the current generator to produce impulses and to monitor the signal of the accelerometer, increasing the intensity of the impulses in relation to time, stopping the production of impulses when the signal produced by the accelerometer is detected, which signal is the H-reflex caused by stimulation of the median nerve, saving at least the intensity value of the latest impulse and time $\Delta T$, which is the difference between a time of the signal produced by the accelerometer and a time of the latest impulse, and identifying the H-reflex based on the time $\Delta T$, calculating a value of fatigue based on at least one of said values, and comparing the value of fatigue with a reference value, wherein a difference between said value of fatigue and the reference value indicates a stress level.

18. The method according to claim 17, wherein a size of said value of fatigue and the reference value describes a type of the level of fatigue.

19. The method according to claim 18, wherein the type of the level of fatigue is displayed in a measuring device or in an external device with an arrangement for connection with the measuring device, or in both.

20. The method according to claim 17, wherein the time $\Delta T$ caused by the H-reflex is 10-100 ms.

* * * * *